United States Patent [19]

Ontek

[11] 4,305,279
[45] Dec. 15, 1981

[54] LIQUID SAMPLING APPARATUS

[76] Inventor: Louis S. Ontek, R.D. No. 3, Box 365, Jackson, N.J. 08527

[21] Appl. No.: 156,878

[22] Filed: Jun. 6, 1980

[51] Int. Cl.³ .............................................. G01N 1/12
[52] U.S. Cl. .................................... 73/155; 73/864.63
[58] Field of Search ........... 73/864.51, 864.63, 864.65, 73/864.66, 864.71, 155; 33/126.4 R, 126.4 A

[56] References Cited

U.S. PATENT DOCUMENTS 1,585,072  5/1926  Banks ............................... 73/864.63

FOREIGN PATENT DOCUMENTS 684374  9/1979  U.S.S.R. ............................ 73/864.63
732723  5/1980  U.S.S.R. ............................ 73/864.67

Primary Examiner—S. Clement Swisher
Attorney, Agent, or Firm—Martin Sachs

[57] ABSTRACT

A liquid sampling apparatus for use in sampling the liquid in a well pipe to determine the surface contaminants contained therein includes an elongated hollow housing for insertion into the well pipe which is adapted to be lowered into the well by means of a flexible line affixed thereto. The other end of the flexible line is affixed to the removable well cap. Disposed above the lower edge of the hollow housing is a valve which includes a cup-shaped closure adapted to cooperate with and seal an opening provided in the bottom thereof by means of the weight of the liquid trapped in the sampling apparatus as it is lifted out of the well pipe.

10 Claims, 4 Drawing Figures

LIQUID SAMPLING APPARATUS

BACKGROUND OF THE INVENTION

1. Field of the Invention

The present invention relates to liquid sampling devices, and in particular, to a liquid sampling apparatus which may be used to obtain samples of contaminants appearing on the surface of well water and directly beneath the surface thereof.

2. Discussion of the Relevant Art

The art abounds with devices which are used to sample liquids to determine their density, amount of contamination, etc. Generally, these devices disclose a valve which is sealed by the weight of the liquid sample contained in the container. Typical of these devices is U.S. Pat. No. 2,447,861 issued to Junge, which discloses a ball type closure mechanism that seals an opening provided in the base thereof. The ball is released when the sampling device reaches the bottom of the container and the string from which the device is suspended is allowed to slacken. The ball falls into position by the weight of gravity and is held there by the weight of the liquid in the device as the device is raised out of the fluid from which the sample has been obtained. Another device is disclosed in U.S. Pat. No. 1,585,072 issued to Banks. The apparatus disclosed therein includes a bottom flat plate which cooperates with a packing material thereby providing a seal holding the oil sample within the chamber. The flat plate functions as a valve and is disposed proximate the bottom opening.

Another device which is used as a liquor tester is disclosed in U.S. Pat. No. 164,451 issued to Hellen. Here a flapper type of valve is utilized to retain a liquid sample within the housing. One edge of the flat flapper is hingedly affixed to a circumferentially disposed lip portion and is caused to move in a downwardly direction sealing the opening when the device is removed from the liquid being sampled.

Generally, these devices are complicated mechanisms and require one or more movements of a string or contact with the bottom surface of a container for operation. These devices are not suitable to obtain samples of contamination appearing on the surface of liquids. Moreover, as these devices enter the liquid from which a sample is to be obtained, they generally disturb the surface thereby providing erroneous results by not including the liquids that may be floating on the surface of which the sample is to be taken. Moreover, the relatively simple devices discussed above may easily be rendered ineffective by dirt, or other particles which may enter the opening of the valve preventing the proper seating of the valve closing mechanisms.

SUMMARY OF THE INVENTION

Therefore, it is an object of the present invention to provide a relatively simple liquid sampling device that is reliable and easy to operate.

Another object of the present invention is to provide a liquid sampling device that is capable of obtaining a sample of liquid at the surface thereof, without disturbing any contaminants which may be floating thereon.

It is yet another object of the present invention to provide a liquid sampler which can sample liquid at any desired location below the surface in a well and which is easy to operate, easy to carry, and economical to manufacture.

It is still another object of the present invention to provide a liquid sampling apparatus that may readily be stored in a well pipe and is removably affixed to the well cap, thereby making it available whenever required.

Still another object of the present invention is to provide a liquid sampling apparatus that is simple to manufacture and is reliable by providing means for self-cleaning any particles out of the valve portion during use.

It is a further object of the present invention to provide a liquid sampling apparatus that overcomes the shortcomings of the devices known in the prior art.

A liquid sampling apparatus, according to the principles of the present invention, for use in a well pipe having a removable cap comprises an elongated hollow housing means for insertion into the well pipe. The internal diameter of the well pipe is larger than the outer diameter of the hollow housing means. The housing means is provided with a retaining means for retaining one end of a flexible line therein. Also included is a valve means having an outside diameter smaller than the inside diameter of the hollow housing means and which is adapted to be received therein. The valve means includes a hollow valve means housing which has an opened end and a closed end. The closed end is provided with an aperture leaving an internally extending ledge portion circumscribing the internal circumference of the valve means housing. A cup-shaped closure means is disposed within the valve means housing. The closure means has an opening greater than the aperture and essentially disposed thereover for cooperation therewith. In addition, a restraining means is disposed remote from the valve means open end for preventing the cup-shaped closure means for rising in the hollow housing when liquid enters the valve means aperture. The restraining means prevents the cup-shaped closure means from being inverted so that the closure opening is unable to operate with said valve means aperture. O-ring means are disposed about the circumference of the valve means. The valve means is retained in the hollow housing means by the frictional or pressure forces exerted by the O-ring on the valve means and the housing means when the valve means is inserted therein.

The foregoing and other objects and advantages will appear from the description to follow. In the description, reference is made to the accompanying drawing which forms a part hereof, and in which is shown by way of illustration the specific embodiment in which the invention may be practiced. This embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawing in which.

DESCRIPTION OF THE PREFERRED EMBODIMENTS

Figure 1:
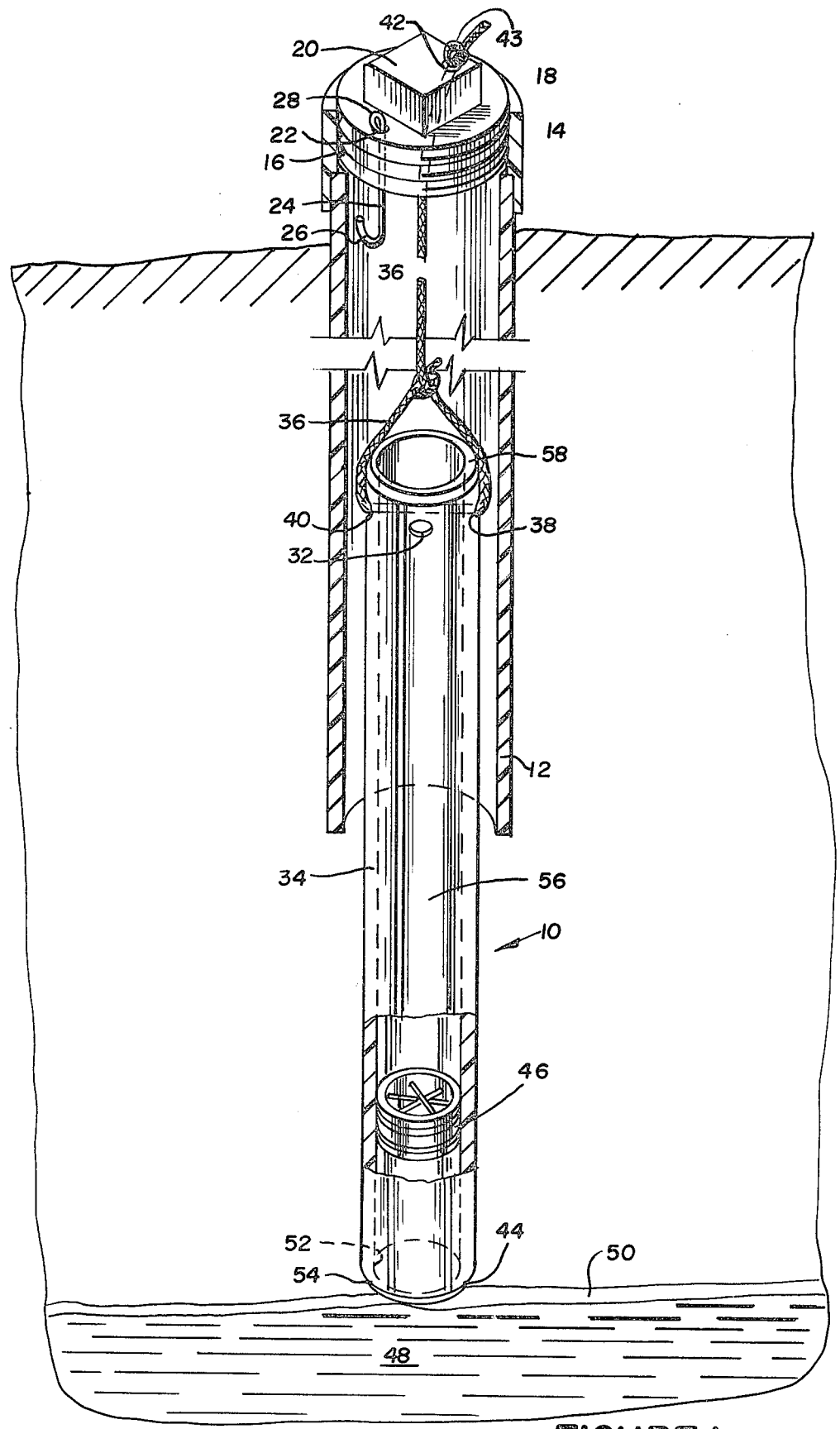
FIG. 1 is a pictorial representation of a well pipe embedded in the ground with a well cap thereon and a liquid sampling apparatus partially shown in cross-section, according to the principles of the present invention.

Referring now to the figures, and in particular to FIG. 1, wherein a liquid sampling apparatus 10 is shown positioned within a conventional well pipe fabricated from polyethylene, polyvinyl chloride, or any other suitable material. The well pipe sections may be connected together by means of couplers, not shown, and held by an adhesive such as acetone, in a conventional manner. The well pipe 12 is provided with a well topping 14 which is adhesively affixed to the well pipe 12 and retained thereon in a conventional manner. The well topping 14 is provided with interior threads 16 which are adapted to cooperate with the external threads provided on a well cap 18.

The well cap 18 is preferably provided with a rectangular shaped extending portion 20 which preferably is rectangular, as shown, or hexagonal in shape so that a wrench may be applied thereto for easy removal of the well cap from the well topping by an individual who is to use the liquid sampling apparatus 10. The well cap 18 is also provided with an aperture 22 proximate the circumference thereof. A retaining device 24, which in the preferred embodiment has a hooked portion 26 extending downwardly from the cap 18 into the well pipe 12 and a bent or rounded portion 28 which is larger than the aperture 22 thereby retaining the retaining device 24 in the cap 18.

The hooked shaped portion 26 of the retaining device 24 is adapted to cooperate with an aperture 32 provided on the liquid sampling apparatus housing 34 which preferably is elongated and is tubular-shaped. Preferably the housing 34 is made of a material which is transparent, such as lucite, or other suitable materials so that the sampling liquid may be viewed by an individual when it is removed from the well. The housing 34 is preferably made two to three feet long and its exact length depends upon the diameter utilized and the amount of sample liquid to be obtained and, of course, has an outer diameter which is smaller than the inner diameter of the well pipe into which it is to be inserted to obtain the sample. The upper portion of housing 34 is provided with a means for retaining a flexible line or rope 36 therein. In the preferred embodiment, this is accomplished by providing a pair of inline apertures 38 and 40 through which the rope 36 may be passed and is knotted as shown just above the housing 34 thereby affixing the rope to the housing in a simple, convenient manner without utilizing any adhesives or other contaminating materials. The rope 36 is preferably passed through an aperture 42 provided in the well cap 18. Here again, a retaining device is utilized to prevent the rope from sliding back through aperture 42 and in the peferred embodiment merely consists of a knot 43 provided proximate the end of the rope 36. Thus, if by accident, the liquid sampling apparatus is dropped by the individual attempting to take a sample, it will not fall into the well and be unretreivable. The well cap being slightly larger than the well pipe and threaded therein will prevent the sampling apparatus from falling into the well with the rope 36.

When the sampling apparatus is to be stored for future use, it may be raised up out of the well and aperture 30 or 32 placed over a portion 26 of the retaining device 24 provided in the cover 18. Thus, it will remain proximate the well cap as the well cap is threaded onto the well topping thereby sealing the well from any foreign contaminants.

Spaced at approximately two to five inches from the lower end portion 44 of the housing 34 is a valve 46 force fit into the opening of housing 34. The construction of the valve 46 will be described in further detail hereinafter. Preferably, the valve is positioned between two and six inches (5.08–15.25 cm) from the lower edge 44 of the housing 14. Ideally, it is placed between two to three inches (5.08–7.62 cm) from the lower edge of the housing in order to avoid disturbing any contaminants appearing on the surface of the water as it is lowered into the well. The water 48 which may have a fine coating or sheen 50 floating thereon will rise into the lower opening 52 provided in the housing 34 and since lower edge 44 is provided with a champer 54, the coating 50 is not disturbed as the housing 34 is lowered into the water 48. Therefore, the sample obtained in the sampling apparatus 10 will clearly reflect what appears on the surface and in the water being sampled. The sample water with its associated contaminants will flow upwardly through valve 46 and fill the upper portion 56 of the housing 34 and is not permitted to overflow the upper edge of the housing 34. The depth of sampling may readily be determined by experimentation by one experienced in obtaining such samples. An individual experienced in obtaining samples may readily discern when the sampling device has entered the water and will limit the further travel of the sampling device 10 so that the sample of liquid will not overflow the housing 34. As the liquid sampling apparatus 10 is raised out of the water a valve 46 will close retaining the water in the housing 14 which may be observed by the individual when he pulls the sampling apparatus out of the well pipe.

Figure 2:
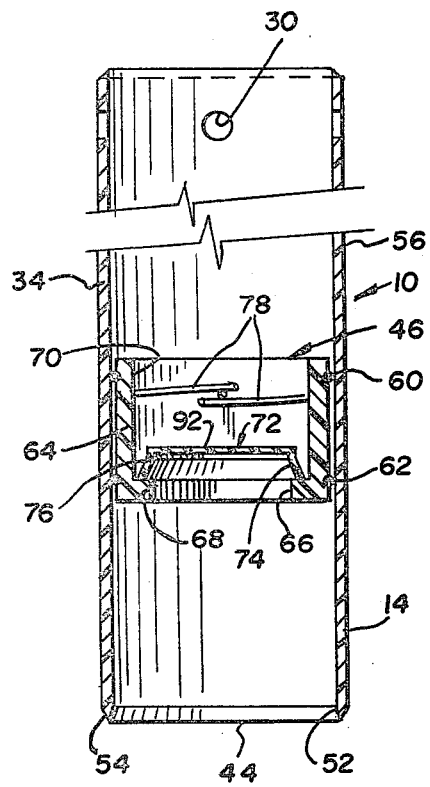
FIG. 2 is an enlarged cross-sectional view of a liquid sampling apparatus with its associated valve.

Referring now to FIG. 2, it will become apparent how the valve 46 is caused to close by the weight of the liquid contained in the housing 14. The valve 46 has an outside diameter which is smaller than the inside diameter of the housing 34. And is held therein by the frictional and pressure forces which occur on O-rings 60 and 62 circumscribing the outer diameter of the hollow housing 64 of the valve 46. The lower portion of the housing 64 is provided with an aperture 66 which is smaller than the inner diameter of the housing 64 thereby providing an internally extending ledge portion 68 circumscribing the internal circumference 70 of the valve housing 64.

A cup-shaped valve closure device 72 is positioned within the internal diameter 72 in an inverted position. That is to say, the opening 74 of the cup-shaped closure device 72 is faced in a downwardly direction and is larger in size than the aperture 66 provided in the lower portion of valve housing 64. Preferably, the cup-shaped closure device 72 has sloping side walls 76 which are capable of flexing so that they can come into contact with the internal circumference 70 of the housing valve 64 under the weight of the liquid 48 when in the upper portion 56 of the housing 34. The cup-shaped closure 72 cooperates with the aperture 66 providing a seal thereto preventing any liquid appearing in the upper portion 56 from leaving aperture 66 through which it entered when the sampling apparatus 10 was placed into the well liquid.

Figure 4:
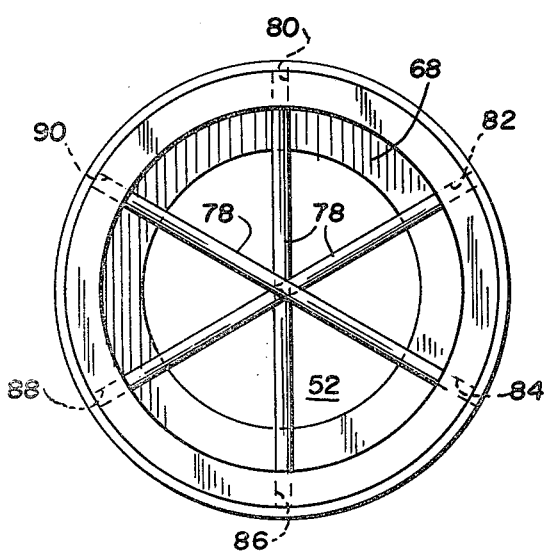
FIG. 4 is a plan view taken along the lines 4—4 as shown in FIG. 3.

Disposed a relatively short distance above the closure device 72 are a plurality of rods which extend across the diameter of the valve housing and are inserted into a plurality of apertures 80, 82, 84, 86, 88 and 90, provided in the wall of the valve housing 64 (see FIG. 4). The rods 78 function to permit the cup-shaped closure device 72 to float upon liquid as it enters the upper portion 56 of housing 34 a sufficient height to allow free flow of liquid therethrough, but prevent the closure device from rising and remain floating on the top of the fluid because of air which may be trapped therein. The rods 78 are positioned to further prevent the cup-shaped closure device 72 from tilting or becoming inverted as the fluid rushes into the upper portion 56 of the housing 34 so that when the liquid sampling apparatus 10 is lifted out of the liquid the weight of the liquid in the upper portion of the housing 56 will act on the upper surface 92 of the closure device 72 thereby placing it in position above the aperture 66. The weight of the liquid will further cause the side walls 76 of the closure device to come into contact with the internal circumference of the housing 64 thereby completing the seal of aperture 66 preventing any leakage therefrom.

The valve 46 is forced into the opening 52 and positioned as indicated earlier without the use of any adhesive to maintain it in position. Thus, conventional devices which utilize glue or other holding means which may contaminate the water sample taken from the well is not a problem with the construction utilized in the instant invention. The O-rings 60 and 62 are preferably positioned in grooves provided proximate the upper and lower edges of the valve housing 64 so that they are retained in position when inserted into the opening 52 of the housing 34.

Figure 3:
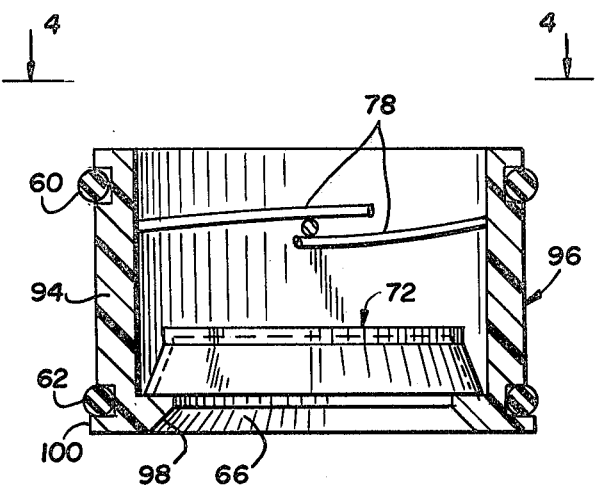
FIG. 3 is an enlarged cross-sectional view in elevation of an alternate embodiment of the valve portion of the liquid sampling apparatus.

In the embodiment shown in FIG. 3, which is an enlarged cross-sectional view of a construction which is similar to the embodiment shown in FIG. 2, like numerals have been given to like components for clarity. The housing 94 of the valve 96 is similar to the valve 46 shown in FIG. 2 with the exception that the aperture 66 is provided with a sloped wall 98 to reduce any turbulence that may occur as the liquid flows through the valve 96 and will be required if small amounts of turbulence can not be tolerated. In addition, a small protruding external lip 100 circumscribes the outer diameter of housing 94 when it is to be inserted into the opening 52 of housing 34. The lip 100 is utilized when relatively large valves such as those exceeding three inches in diameter are to be utilized in order to maintain O-ring 62 in position when the valve housing 96 is inserted into the housing 34.

FIG. 4 is a top view of the embodiment shown in FIG. 3 and will also serve as a top view for the embodiment shown in FIG. 2, since they would effectively be the same.

In operation, the liquid sampling apparatus of the instant invention is retained on the hooked portion 26 of retaining device 24 with the well cap screwed into place in the well topping 14 thereby sealing the well pipe. An individual desiring to obtain a sample of the liquid in the well would remove the well cap by unthreading it from the well topping and raise it upwardly, thereby drawing the liquid sampling apparatus 10 out of the well pipe. The line or rope 36 will have been permitted to fall downwardly within the spacing between the inner diameter of the well pipe and the outer diameter of the housing 34. Once the cap 18 has been removed, the liquid sampling apparatus is slowly lowered into the well until it reaches the water therebelow. Once the sampling apparatus has had sufficient time to permit the liquid to flow into the housing 34, the housing 34 is raised out of the well and may be viewed by the individual obtaining the sample or the liquid contained in the housing may be poured into another container for evaluation at a laboratory.

The construction of the valve utilized in the sampling apparatus is simple, efficient, and is effectively self-clearing so that any debris or particles of dirt which might enter the valve will readily be washed therefrom as the liquid is poured out of the housing 34. With the sampling apparatus taken out of the well, a gentle tapping of the housing will cause any particles of dirt which may have entered into the valve to fall freely therefrom.

Hereinbefore has been disclosed a simple, reliable liquid sampling apparatus which may be used to obtain liquid samples from relatively narrow well piping. It will be understood that various changes in the details, materials, arrangement of parts and operating conditions which have been herein described and illustrated in order to explain the nature of the invention may be made by those skilled in the art within the principles and scope of the present invention.

Having thus set forth the nature of the invention, what is claimed is:

1. A liquid sampling apparatus for use in a well pipe having a removable cap comprising:
   (a) an elongated hollow housing means for insertion into said well pipe, the internal diameter of said well pipe being larger than the outer diameter of said hollow housing means, said housing means being provided with a retaining means for retaining one end of a flexible line therein; and
   (b) valve means having an outside diameter smaller than the inside diameter of said hollow housing means and adapted to be received therein and including;
     (i) a hollow valve means housing having an open end and a closed end, said closed end being provided with an aperture leaving an internally extending ledge portion circumscribing the internal circumference of said valve means housing,
     (ii) cup-shaped closure means disposed within said valve means housing, said closure means having an opening greater than said aperture and being centrally disposed thereover for cooperation therewith,
     (iii) restraining means disposed remote from said valve means open end for preventing said cup-shaped closure means from rising in said hollow housing when liquid enters said valve means aperture, said restraining means preventing said cup-shaped closure means from being inverted so that said closure opening is unable to cooperate with said valve means aperture, and
     (iiii) O-ring means disposed about the circumference of said valve means, said valve means being retained in said hollow housing means by the frictional and pressure forces exerted by said O-ring on said valve means and said housing means when said valve means is inserted therein.

2. A liquid sampling apparatus according to claim 1 wherein said pipe cap is provided with a means for retaining said housing means proximate thereto when capping said well pipe.

3. A liquid sampling apparatus according to claim 2 wherein said pipe cap retaining means is hook-shaped, affixed to said cap and adapted to cooperate with an aperture provided in said housing means proximate the upper edge thereof.

4. A liquid sampling apparatus according to claim 1 wherein said pipe cap is provided with means for retaining the other end of said flexible link.

5. A liquid sampling apparatus according to claim 1 wherein the opening of said cup-shaped closure means has an outside diameter sufficiently large to reach the internal diameter of said valve means housing when removed from said well and acted upon by the weight of said liquid in said housing means.

6. A liquid sampling apparatus according to claim 1 wherein said valve means closed end is disposed between 2.0 and 6.0 inches (5.08–15.25 cm) from the lower edge of said housing means.

7. A liquid sampling apparatus according to claim 1 wherein said valve means closed end is disposed between 2 to 3 inches (5.08–7.62 cm) from the lower edge of said housing means.

8. A liquid sampling apparatus according to claim 1 wherein said cup-shaped closure means is fabricated from neoprene.

9. A liquid sampling apparatus according to claim 1 wherein said restraining means includes a plurality of rods inserted into apertures disposed above said valve means closed end and remote therefrom, said apertures being spaced about the circumference of said valve means.

10. A liquid sampling apparatus according to claim 1 wherein a pair of O-rings are utilized, one O-ring being disposed proximate each end of said valve means.

* * * * *